United States Patent
Mallard et al.

(10) Patent No.: US 10,849,854 B2
(45) Date of Patent: Dec. 1, 2020

(54) PROCESS FOR PREPARING A COMPOSITION COMPRISING A HIGH CONCENTRATION OF ONE OR MORE AVERMECTINS

(71) Applicant: GALDERMA SA, Cham (CH)

(72) Inventors: Claire Mallard, Mougins (FR); Elodie Roger, Cagnes-sur-mer (FR)

(73) Assignee: GALDERMA S.A., Cham (CH)

( * ) Notice: Subject to any disclaimer, the term of this patent is extended or adjusted under 35 U.S.C. 154(b) by 0 days.

(21) Appl. No.: 15/767,079

(22) PCT Filed: Oct. 13, 2016

(86) PCT No.: PCT/EP2016/074626
§ 371 (c)(1),
(2) Date: Apr. 9, 2018

(87) PCT Pub. No.: WO2017/064206
PCT Pub. Date: Apr. 20, 2017

(65) Prior Publication Data
US 2018/0296482 A1    Oct. 18, 2018

(30) Foreign Application Priority Data

Oct. 13, 2015 (EP) .................... 15306620

(51) Int. Cl.
| | | |
|---|---|---|
| *A61K 9/107* | (2006.01) |
| *A61K 9/06* | (2006.01) |
| *A61K 31/7048* | (2006.01) |
| *A61K 9/10* | (2006.01) |
| *A61P 17/10* | (2006.01) |
| *A61P 17/08* | (2006.01) |

(52) U.S. Cl.
CPC ............... *A61K 9/107* (2013.01); *A61K 9/06* (2013.01); *A61K 9/10* (2013.01); *A61K 31/7048* (2013.01); *A61P 17/08* (2018.01); *A61P 17/10* (2018.01)

(58) Field of Classification Search
CPC ...... A61K 31/7048; A61K 9/107; A61K 9/06; A61P 17/08; A61P 17/10
USPC ........................................... 514/32
See application file for complete search history.

(56) References Cited

U.S. PATENT DOCUMENTS

| | | |
|---|---|---|
| 4,870,103 A | 9/1989 | Roechling et al. |
| 2009/0035338 A1 | 2/2009 | Segura-Orsini et al. |
| 2009/0136574 A1* | 5/2009 | Diaz-Astruc ........ A61K 9/0014 424/484 |
| 2009/0227668 A1 | 9/2009 | Manetta et al. |

FOREIGN PATENT DOCUMENTS

| | | |
|---|---|---|
| CN | 1957701 A | 5/2007 |
| CN | 104273142 A | 1/2015 |
| CN | 104738031 A | 7/2015 |
| WO | 2004/093886 A1 | 11/2004 |
| WO | WO-2007/119028 A2 | 10/2007 |

OTHER PUBLICATIONS

Tippetts (Thesis: "Effect of Processing and Formulation Conditions on Physicochemical Characteristics of Food Emulsions" by Megan Tippetts, Master of Science, Utah State University; 2008, i-xii, 1-122).*
International Search Report dated Jan. 24, 2017 corresponding to International Patent Application No. PCT/EP2016/074626, 4 pages.
Written Opinion of the International Searching Authority dated Jan. 24, 2017 corresponding to International Patent Application No. PCT/EP2016/074626, 5 pages.
International Search Report and Written Opinion issued in International Patent Application No. PCT/EP2016/074624 dated Feb. 8, 2017 (8 pages).

* cited by examiner

*Primary Examiner* — Shaojia A Jiang
*Assistant Examiner* — Michael C Henry
(74) *Attorney, Agent, or Firm* — Foley & Lardner LLP; Sunit Talapatra

(57) ABSTRACT

A process is described for preparing a composition in the form of an emulsion that includes a high concentration of one or more avermectins. This process can include partitioning the avermectin between an active phase, including at least one glycol, and an oily phase of the emulsion. A composition thus obtained, is also described that can be used in the treatment of dermatological disorders such as rosacea.

17 Claims, No Drawings

PROCESS FOR PREPARING A COMPOSITION COMPRISING A HIGH CONCENTRATION OF ONE OR MORE AVERMECTINS

CROSS-REFERENCE TO PRIOR APPLICATIONS

This application is a National Stage of PCT/EP2016/074626 filed Oct. 13, 2016, and designating the United States (published on Apr. 20, 2017, as WO 2017/064206 A1), which claims priority under 35 U.S.C. § 119 to European Patent Application No. 15306620.4, Oct. 13, 2015, each hereby expressly incorporated by reference in its entirety and each assigned to the assignee hereof.

FIELD OF THE INVENTION

The present invention pertains to a process for preparing a composition comprising a high concentration of one or more avermectins. It is also directed to the composition thus obtained, especially for use in the treatment of dermatological disorders such as rosacea.

BACKGROUND OF THE INVENTION

Avermectins are macrocyclic lactones having potent antihelmintic and insecticidal properties, which are obtained by fermentation of *Streptomyces avermitilis*, a soil actinomycete. Among avermectins, mention can be made of ivermectin, selamectin, doramectin and abamectin. Ivermectin is itself a mixture of two compounds, namely 5-O-demethyl-22,23-dihydroavermectin A1a and 5-O-demethyl-22,23-dihydroavermectin A1b. They are also known under the trademarks of 22,23-dihydroavermectin B1a and 22,23-dihydroavermectin B1b. Ivermectin comprises at least 80% of 22,23-dihydroavermectin B1a and less than 20% of 22,23-dihydroavermectin B1b.

In the middle of the 1980s, ivermectin was presented as a broad-spectrum anti-parasitic medicament for veterinary use, as it is effective against the majority of common intestinal worms (except for the Teniae), the majority of the acarids and a few lice. In humans, ivermectin is more particularly used as an anthelmintic, in the treatment of onchocerciasis due to *Onchocerca volvulus*, of gastrointestinal strongyloidiasis (anguillulosis) and of human scabies. More recently, it has been suggested to use ivermectin for the treatment of dermatological disorders such as rosacea (WO 2004/093886). A cream comprising 1% ivermectin has been approved by the FDA for the topical treatment of inflammatory lesions of rosacea (Soolantra®).

In the case where ivermectin is formulated for topical application, it is advantageous to incorporate it in an emulsion which may be easily spread onto skin. However, ivermectin is unstable in the presence of water, which can result in chemical instability of the active principle and/or in crystallization of the initially dissolved active principle. In addition to a loss of effectiveness of the active principle, this may in turn detrimentally affect the overall stability of the compositions containing ivermectin, including their viscosity and their appearance. In order to reduce or prevent this phenomenon, it has been suggested to dissolve ivermectin in suitable solubilizers, such as mixture of propylene glycol and oleyl alcohol, so as to form an active phase which may then be added to an oil-in-water emulsion stabilized either with a polymeric emulsifier (FR 2 867 684), or with a surfactant (U.S. Pat. No. 8,080,530). Another solution was provided in U.S. Pat. No. 8,287,891, which consists in formulating ivermectin in an inverse emulsion wherein a significant portion of the aqueous phase is replaced with glycols, so as to obtain a glycol-in-oil emulsion.

Although these prior attempts have allowed formulating ivermectin in emulsions which remain stable despite temperature and/or pH variations, it has been observed that the amount of ivermectin that could be introduced into these emulsions was limited. Specifically, at most 33% by weight of ivermectin can be fully dissolved in a mixed propylene glycol/oleyl alcohol (1/1) solubilizing medium. Beyond this concentration, ivermectin tends to crystallize in the active phase before the emulsion is prepared and/or in the resulting emulsion, optionally when subjected to freeze/thaw cycles. Increasing the amount of glycols in the emulsion would raise other issues, since the emulsion stability would be detrimentally affected and the emulsion would become too sticky to be commercially acceptable. Therefore, from a practical point of view, it has not been possible so far to formulate emulsions comprising 2% or more by weight of ivermectin, which remains fully dissolved ivermectin over the time.

In view of the foregoing, there remains the need for a stable emulsion over the time comprising 2% or more by weight, of one or more avermectins, such as ivermectin.

SUMMARY OF THE INVENTION

The Applicant has now surprisingly found that a composition in the form of an emulsion comprising 2% or more by weight of at least one avermectin, relative to the total weight of the composition, may be obtained according to a process comprising adding an active phase containing at least one glycol into an emulsion comprising an aqueous phase and an oily phase, provided that said avermectin is distributed between the active phase and the oily phase of the emulsion.

The present invention is directed to a process for manufacturing a composition in the form of an emulsion comprising 2% or more by weight of at least one avermectin relative to the total weight of the composition, wherein such at least one avermectin is completely solubilized.

Thus, this invention is directed to a process for manufacturing a composition in the form of an emulsion comprising at least one avermectin, comprising the following successive steps:
(a) preparing an oily phase and an aqueous phase,
(b) emulsifying said oily and aqueous phases in order to obtain an emulsion,
(c) adding to said emulsion an active phase containing from 0.05 to 3%, preferably from 0.1 to 2% by weight of at least one avermectin, relative to the total weight of the composition, which is dissolved in a medium comprising at least one glycol, characterized in that step (a) comprises adding from 0.05 to 3%, preferably from 0.1 to 2% by weight of said at least one avermectin into the oily phase.

The present invention is also directed to a composition in the form of an emulsion comprising 2% or more by weight of at least one avermectin relative to the total weight of the composition, characterized in that said composition is stable over the time, such that the avermectin compound is completely solubilized in the composition during and after manufacturing said composition, for instance after two months storage at 5° C. and/or two weeks freeze-thaw cycles between −18° C. and 25° C.

More precisely, this invention is also directed to a composition in the form of an emulsion comprising an active phase and an aqueous phase both dispersed in an aqueous phase, wherein the active phase comprises from 0.05 to 3%, preferably from 0.1 to 2% by weight of at least one avermectin, relative to the total weight of the composition, characterized in that the oily phase includes from 0.05 to 3%, preferably from 0.1 to 2% by weight of said at least one avermectin, relative to the total weight of the composition.

It is also directed to the above composition for use in the treatment of a dermatological disorder such as rosacea, atopic dermatitis, hand eczema, common acne, seborrheic dermatitis, perioral dermatitis, acneiform rashes, transient acantholytic dermatosis and acne necrotica miliaris, preferably rosacea.

DETAILED DESCRIPTION

The manufacturing process of this invention comprises a first step of preparing an oily phase and an aqueous phase.

The aqueous phase may comprise from 30 to 95%, and preferably from 60 to 80% by weight of water, relative to the total weight of the composition. In addition, it may include at least one of: a gelling agent, such as carboxyvinyl polymers (Carbomers), cellulose derivatives, polysaccharide gums, homo- and copolymers of acrylamide, of alkyl acrylate, of acrylic acid, and/or of 2-acrylamido-2-methylpropane sulfonic acid (AMPS), clays and native or modified starches; a polyol such as glycerin; a chelating agent; a pH adjusting agent; and mixtures thereof. Preferably, at least one gelling agent is included within the aqueous phase.

The oily phase may comprise at least one oil, which may be selected from vegetable, mineral, animal and/or synthetic oils, such as alkyl esters, silicone oils, paraffin oils and mixtures thereof. In addition, the oily phase may include at least one thickening agent which may be selected from linear fatty alcohols, for instance stearyl and/or cetyl alcohol, linear fatty acids, vegetable waxes, silicone gums and mixtures thereof. Preferably, at least one linear fatty alcohol, comprising from 12 to 20 carbon atoms, is included within the oily phase. The ingredients of the oily phase may be selected in a varied manner by those skilled in the art in order to prepare a composition having the desired properties, for example of consistency or of texture. The oily phase may represent from 3 to 50%, preferably from 10 to 20% by weight, relative to the total weight of the composition.

The process of this invention is characterized in that at least one avermectin is included in the oily phase during its preparation, in an amount of from 0.05 to 3%, preferably from 0.1 to 2% by weight, and even more preferably from 0.25 to 1% by weight, relative to the total weight of the composition that is being prepared.

Examples of avermectins include: invermectin, ivermectin, avermectin, abamectin, doramectin, eprinomectin, selamectin and optical isomers thereof. According to a preferred embodiment of this invention, said avermectin is selected from ivermectin and optical isomers thereof.

The aqueous and/or oily phase may further include at least one of: a preservative such as an alkyl parahydroxybenzoate (paraben), phenoxyethanol and mixtures thereof; an antioxidant; an emulsifier such as a sorbitan ester, a polyoxyethylene ether of fatty alcohol, a polyoxyethylene fatty acid ester, a glyceryl ester; and mixtures thereof. Preferably, at least one non-ionic surfactant is included within the oily phase In the second step of the process according to this invention, said oily and aqueous phases are emulsified, usually by introducing the oily phase into the aqueous phase under stirring.

According to a preferred embodiment of this invention, this emulsification step is performed at a temperature between 60 and 75° C., preferably of from 60 to 70° C., and still preferably at a temperature of 65° C.±2° C. It is preferred that both the aqueous and oily phases are heated to said temperature before mixing. Such pre-heating steps may be initiated at any stage during the preparation of the aqueous and oily phases. It will be readily apparent for the skilled artisan which constituents should be added prior to heating and which should be added only after. The resulting oil-in-water emulsion is then cooled down to a temperature of from 48 to 55° C., preferably at 50° C.±2° C.

Then, an active phase containing said at least one avermectin dissolved in a medium comprising at least one glycol is introduced into said emulsion. The active phase is preferably heated to the same temperature as the emulsion before introducing the former into the latter. This pre-heating step may be initiated at any stage during the preparation of the active phase and preferably before adding the avermectin therein.

The active phase usually contains from 0.05 to 3%, preferably from 0.1 to 2% by weight, by weight of avermectin, relative to the total weight of the composition.

The glycol may represent from 0.5 to 15% by weight, and preferably from 1 to 8% by weight, relative to the total weight of the composition. Examples of glycols are (C1-C6) alkylene glycols and poly(C1-C6) alkylene glycols, such as ethylene glycol, propylene glycol, polyethylene glycol, polypropylene glycol, butylene glycol, pentylene glycol and hexylene glycol and their mixtures. A preferred glycol is propylene glycol. The glycol may be mixed with one or more monohydric alcohols selected from C1-C6 monohydric alcohols, such as ethanol, isopropanol and butanol, C12 to C32 linear unsaturated or branched saturated monohydric alcohols, such as oleyl alcohol or Guerbet alcohols, polyhydric alcohols other than glycols, such as glycerol; and mixtures thereof. According to an embodiment of this invention, the active phase comprises a mixture of propylene glycol and oleyl alcohol in a weight ratio of from 1:4 to 4:1 and preferably of 1:1. According to an embodiment, the active phase represents from 1 to 18% of the total weight of the composition.

An emulsion is thus obtained, which is advantageously cooled, in the next step of the process according to this invention, to a target temperature of from 30 to 40° C., preferably at 35° C.±2° C., by subjecting said emulsion to controlled cooling to said target temperature.

This embodiment of the invention allows improving the stability of the composition and especially avoiding large viscosity changes immediately after manufacture. Without being bound by this theory, it is assumed that this increase in viscosity is due to the swelling in water of lamellar structure formed by the non-ionic surfactants and fatty alcohols initially present in the oily phase, once both phases have been brought together and cooled.

According to an embodiment, said controlled cooling comprises, or preferably consists in, cooling said emulsion at a cooling rate of from 0.5 to 1.5° C./5 min, preferably from 0.8 to 1.5° C./5 min and more preferably of 1° C./5 min, usually with a temperature regulation system.

According to another embodiment, said controlled cooling comprises, and preferably consists in, cooling said emulsion to a temperature comprised between 42 and 47° C., then maintaining a temperature plateau, preferably for 10 to 20 minutes, and further cooling said emulsion to said target temperature.

These cooling steps are preferably performed while stirring the emulsion.

The resulting emulsion may then be further cooled to room temperature, i.e. from 20 to 25° C., optionally after adding a neutralizing agent, such as a base, to the emulsion (which may be required in the case where the gelling agent bears acidic groups, for instance when a Carbomer is used).

A composition is thus obtained, which may comprise from 0.1 to 6% by weight of avermectin and preferably from 2% to 3% by weight of avermectin, relative to the total weight of the composition, such composition being stable over the time.

In the case where a controlled cooling step is included in the preparation process, as described above, the viscosity of this composition, when stored at room temperature for 7 days immediately after manufacturing, does not vary by more than 10%, preferably by no more than 5%. Such viscosity may be measured at room temperature (20-25° C.) by a Brookfield viscosimeter RV DVII equipped with a #34 spindle rotating at 6 rpm.

This composition may be used in the treatment of a dermatological disorder such as rosacea, atopic dermatitis, hand eczema, common acne, seborrheic dermatitis, perioral dermatitis, acneiform rashes, transient acantholytic dermatosis and acne necrotica miliaris, preferably rosacea.

EXAMPLES

This invention will be better understood in light of the following examples which are given for illustrative purposes only and do not intend to limit the scope of the invention, which is defined by the attached claims. In the following examples, the process according to the present invention is named Process A. The process of example 2 is named Process B.

Example 1: Preparation of Creams with 2.25% and 3% Ivermectin with Process A

The compositions described in table 1 below were prepared according to the following process A as a 1 kg batch.

TABLE 1

| PHASE | INCI NAME | 2.25% W/W | 3% W/W |
|---|---|---|---|
| OILY PHASE | ISOPROPYL PALMITATE | 4.0 | 4.0 |
| | CETYL ALCOHOL | 3.5 | 3.5 |
| | STEARYL ALCOHOL | 2.5 | 2.5 |
| | CETEARETH-20 | 3.0 | 3.0 |
| | SORBITAN MONOSTEARATE | 2.0 | 2.0 |
| | DIMETHICONE | 0.5 | 0.5 |
| | PROPYL PARAHYDROXY-BENZOATE | 0.1 | 0.1 |
| | IVERMECTIN | 0.25 | 1.0 |
| AQUEOUS PHASE | CARBOMER COPOLYMER TYPE B | 0.2 | 0.2 |
| | GLYCERIN | 4.0 | 4.0 |
| | METHYL PARAHYDROXY-BENZOATE | 0.2 | 0.2 |
| | DISODIUM EDTA | 0.05 | 0.05 |
| | CITRIC ACID | 0.05 | 0.05 |
| | PHENOXYETHANOL | 1.0 | 1.0 |
| | WATER | QSP 100 | QSP 100 |
| ACTIVE PHASE | PROPYLENE GLYCOL | 2.0 | 2.0 |
| | OLEYL ALCOHOL | 2.0 | 2.0 |
| | IVERMECTIN | 2.0 | 2.0 |
| NEUTRALIZING AGENT | NAOH 1% SOLUTION | QS pH | QS pH | a) Preparation of the Three Phases:

The water phase was made by dispersing the gelling agent in water in a first tank, under shear until a homogenous gel was obtained. After heating at a temperature comprised between 60° C. and 75° C., preferably 65° ° C.±2° C., glycerol and the remaining constituents of the aqueous phase were added.

The oily phase was made separately by mixing the ingredients in a second tank and heated at a temperature comprised between 60° C. and 75° C., preferably 65° ° C.±2° C. under stirring until the mixture is homogeneous. Ivermectin was weighted in a weighing boat and then added to this tank, which was then stirred until ivermectin was fully dissolved.

The active phase was made by introducing solvents into a third tank, heated at 50° C. and homogenized. Ivermectin was weighted in a weighing boat and then added to this tank, which was then stirred until ivermectin was fully dissolved.

b) Emulsification Step:

When the oily and aqueous phases were at the same temperature, preferably around 65° C. the two phases were mixed under shear for 10 min. The emulsion thus formed was allowed to cool to 50° C., then the active phase was added thereto under shear.

A cooling step was then performed from 50° C. to 35° C. with a temperature plateau at 45° C. during 15 minutes or with a cooling rate of 1° C./5 min with constant shear rate.

A neutralizing agent was then added at 35° C. until the pH was comprised between 6.0 and 6.6 and the composition was further cooled to room temperature. A white to pale yellowish cream was thus obtained.

Example 2: Preparation of Creams with 2.25%, 2.5% and 3.0% of Ivermectin with the Process B The compositions described in table 2 below were prepared on laboratory scale (0.4 and 1 kg batches) according to a similar process to that carried out in example 1.

TABLE 2

| PHASE | INCI NAME | 2% W/W | 2.25% W/W | 3% W/W |
|---|---|---|---|---|
| OILY PHASE | ISOPROPYL PALMITATE | 4.0 | 4.0 | 4.0 |
| | CETYL ALCOHOL | 3.5 | 3.5 | 3.5 |
| | STEARYL ALCOHOL | 2.5 | 2.5 | 2.5 |
| | CETEARETH-20 | 3.0 | 3.0 | 3.0 |
| | SORBITAN MONOSTEARATE | 2.0 | 2.0 | 2.0 |
| | DIMETHICONE | 0.5 | 0.5 | 0.5 |
| | PROPYL PARAHYDROXY-BENZOATE | 0.1 | 0.1 | 0.1 |
| AQUEOUS PHASE | CARBOMER COPOLYMER TYPE B | 0.2 | 0.2 | 0.2 |
| | GLYCERIN | 4.0 | 4.0 | 4.0 |
| | METHYL PARAHYDROXY-BENZOATE | 0.2 | 0.2 | 0.2 |
| | DISODIUM EDTA | 0.05 | 0.05 | 0.05 |
| | CITRIC ACID | 0.05 | 0.05 | 0.05 |
| | PHENOXYETHANOL | 1.0 | 1.0 | 1.0 |
| | WATER | QSP 100 | QSP 100 | QSP 100 |
| ACTIVE PHASE | PROPYLENE GLYCOL | 2.0 | 2.0 | 2.0 |
| | OLEYL ALCOHOL | 2.0 | 2.0 | 2.0 |
| | IVERMECTIN | 2.25 | 2.5 | 3.0 |
| NEUTRALIZING AGENT | NAOH 1% SOLUTION | QS pH | QS pH | QS pH |

The significant differences with the process as described in example 1 being that:
   the aqueous and oily phases were pre-heated at 72° C. and emulsification was performed at this temperature,
   ivermectin was added to the active phase only, and
   the emulsion was cooled from 50° C. to 35° C. within 10 to 20 minutes by leaving it at room temperature, thus at a cooling rate of from 2 to 8° C./5 min.

The main difference with the process of example 1 (Process A) being that ivermectin is only introduced into the active phase and not distributed in the oily phase.

Example 3: Stability Tests of Ivermectin Compositions Obtained by Process a or Process B The emulsions obtained by Process A, where ivermectin has been distributed both in the oily and in the aqueous phases, were observed with a ZEISS microscope, with a magnification of 10×. Ivermectin appeared to be fully solubilized both in the active and in the oily phases. The same held true in the finished product, in which no ivermectin crystals could be observed either.

Conversely, ivermectin crystals were observed in the active phase of the emulsion with 2.25% 2.5% and 3% of ivermectin emulsions prepared by Process B where ivermectin is introduced only in the active phase. After the manufacturing of the ivermectin emulsions according to Process B, ivermectin crystals were observed at 3% in the finished product.

The composition obtained by Process A, containing 2.25% and 3% ivermectin and the compositions obtained by Process B containing 2.25%, 2.5% and 3% ivermectin were further subjected to freeze-thaw cycles (−18° C./+25° C.) during two weeks and subjected to 5° C. storage during 2 months. The aim of this experiment was to evaluate whether ivermectin remained solubilized in the cream under stringent storage conditions. The microscopic observations performed on these creams showed that ivermectin recrystallized after one week under freeze-thaw cycles and after two months under 5° C. storage conditions in the comparative cream (2.5% and 3%,) whereas it remained fully solubilized in the cream prepared according to this invention during the two weeks of freeze-thaw cycles and 2 months 5° C. storage conditions.

Table 3 below presents Freeze/thaw cycles storage conditions that were applied to finished products.

TABLE 3

| Days | 1 to 4 | 5 to 7 | 8 to 10 | 11 to 14 |
|---|---|---|---|---|
| Temperature | −18° C. | 25° C. | −18° C. | 25° C. |

Table 4 below summarizes all the observations made in process and after manufacturing.

TABLE 4

| Ivermectin | In process/Active Phase (s) | | After manufacturing | |
|---|---|---|---|---|
| % w/w | Process A | Process B | Process A | Process B |
| 2.25% | No crystals | Crystals | No crystals | No crystals |
| 2.5% | Not done | Crystals | Not done | No crystals |
| 3.0% | No crystals | Crystals | No crystals | Crystals |

Table 5 below summarizes all the observations made after 2 weeks freeze/thaw cycles and 2 months at 5° C.

TABLE 5

| Ivermectin | Freeze/thaw cycles | | 1 month 5° C. | | 2 months 5° C. | |
|---|---|---|---|---|---|---|
| % w/w | Process A | Process B | Process A | Process B | Process A | Process B |
| 2.25% | No crystals | No crystals | Not reported | No crystals | Not reported | No crystals |
| 2.5% | Not done | Crystals | Not done | No crystals | Not done | Crystals |
| 3.0% | No crystals | Not reported | No crystals | No Crystals | No crystals | Crystals |

These examples demonstrate that the process according to this invention (Process A) allows manufacturing a cream containing a high amount (2% or more by weight) of ivermectin with no crystals observed at any stage of the process, contrary to the comparative process. Therefore this process allows manufacturing a cream physically stable over the time with a high concentration of ivermectin. Therefore, the process of this invention allows a better stability of the composition, which guarantees the quality of the product.

In addition, the viscosity of the composition does not substantially change during the first week after manufacture, which saves the maturation time usually needed. This of course favorably impacts the economics of the process.

Example 4: Physical and Chemical Stability of Ivermectin Cream 3% Obtained by Process A The compositions described in table 6 below were prepared according to Process A on 1 kg batch.

TABLE 6

| PHASE | INCI NAME | 3% W/W Sample A | 3% W/W Sample B |
|---|---|---|---|
| OILY PHASE | ISOPROPYL PALMITATE | 4.0 | 4.0 |
| | CETYL ALCOHOL | 3.5 | 3.5 |
| | STEARYL ALCOHOL | 2.5 | 2.5 |
| | CETEARETH-20 | 3.0 | 3.0 |
| | SORBITAN MONOSTEARATE | 2.0 | 2.0 |
| | DIMETHICONE | | |
| | PROPYL PARAHYDROXYBENZOATE | 0.5 | 0.5 |
| | IVERMECTIN | 0.1 | / |
| | | 1.0 | 1.0 |
| AQUEOUS PHASE | CARBOMER COPOLYMER TYPE B | 0.2 | 0.2 |
| | GLYCERIN | | |
| | METHYL PARAHYDROXYBENZOATE | 4.0 | 4.0 |

TABLE 6-continued

| PHASE | INCI NAME | 3% W/W Sample A | 3% W/W Sample B |
|---|---|---|---|
| | DISODIUM EDTA | 0.2 | / |
| | CITRIC ACID | | |
| | PHENOXYETHANOL | 0.05 | 0.05 |
| | HEXYLENE GLYCOL | 0.05 | 0.05 |
| | WATER | 1.0 / QSP 100 | 1.0 8 QSP 100 |
| ACTIVE PHASE | PROPYLENE GLYCOL | 2.0 | 2.0 |
| | OLEYL ALCOHOL | 2.0 | 2.0 |
| | IVERMECTIN | 2.0 | 2.0 |
| NEUTRALIZING AGENT | NAOH 1% SOLUTION | QS pH | QS pH |

The table 7 below presents physical and chemical characteristics of these emulsions at initial time.

TABLE 7

| | Sample A | Sample B |
|---|---|---|
| Macroscopic aspect | White cream | White cream |
| Microscopic aspect | Liquid crystals from 3 µm to 15 µm/Absence of crystals | Liquid crystals from 3 µm to 10 µm/Absence of crystals |
| pH | 6.17 | 6.37 |
| Viscosity Method: Viscosimeter Brookfield RV dvII + Small sample adaptator Spindle 34 v = 6 rpm | 53973cP | 14400cP |
| Ivermectin assay (%/label claim) | 97.8% (CV 0.2) | 97.7% (CV 0.9) |

The table 8 below presents physical stability at RT (Room Temperature), 5° C. and 40° C. during 3 months:

TABLE 8

| Formulation number | Physical characterizations | T1 M 5° C. | T1 M RT | T1 M 40° C. | T2 M 5° C. | T2 M RT | T2 M 40° C. | T3 M 5° C. | T3 M RT | T3 M 40° C. |
|---|---|---|---|---|---|---|---|---|---|---|
| Sample A | Macroscopic aspect | No change relative to T0 | | | No change relative to T0 | | | No change relative to T0 | | |
| | Microscopic aspect | No change relative to T0 | | | No change relative to T0 | | | No change relative to T0 | | |
| | pH | 6.19 | 6.11 | 6.23 | 6.17 | 6.17 | 6.26 | 6.25 | 6.10 | 6.05 |
| | Viscosity (cP) | 54613 | 53120 | 58240 | 53227 | 53760 | 55787 | 65387 | 52907 | 50987 |
| Sample B | Macroscopic aspect | No change relative to T0 | | | No change relative to T0 | | | No change relative to T0 | | |
| | Microscopic aspect | No change relative to T0 | | | No change relative to T0 | | | No change relative to T0 | | |
| | pH | 6.40 | 6.36 | 6.42 | 6.49 | 6.39 | 6.52 | 6.39 | 6.33 | 6.33 |
| | Viscosity (cP) | 26453 | 18560 | 23147 | 26027 | 17600 | 19200 | 27413 | 16427 | 16107 |

Both formulations from samples A and B with 3% of Ivermectin and are physically stable 3 months at 5° C., RT and even at 40° C. with no crystals appearing over whatever the storage conditions.

The table 9 below presents chemical stability at RT (Room Temperature) and 40° C. during 3 months.

TABLE 9

| Ivermectin titer | T0 | T1M | | T3M | |
|---|---|---|---|---|---|
| (%/T0) | RT | RT | 40° C. | RT | 40° C. |
| Sample A | 97.8% (CV 0.2) | 97.0% (CV0.7) | 96.6% (CV0.7) | 95.5% (CV0.4) | 95.9% (CV0.4) |
| Sample B | 97.7% (CV 0.9) | 97.6% (CV0.1) | 96.5% (CV0,7) | 95.6% (CV0.1) | 95.4% (CV0.2) |

Samples A and B are chemically stable 3 months RT and 40° C.

These examples demonstrate that the process of the invention (process A) allows manufacturing a cream containing a high amount (2% or more by weight) of ivermectin with a good chemical and physical stability for at least 3 months at 5° C., RT and 40° C. contrary to the comparative process B.

Therefore, the process of this invention (process A) allows a better stability of the composition, which guarantees the quality of the product. This of course favorably impacts the economics of the process.

The invention claimed is:

1. A process of manufacturing a composition in the form of an emulsion comprising at least one avermectin, the process comprising, successively:
   (a) emulsifying an oily phase comprising from 0.05% to 3% by weight of the at least one avermectin, relative to the total weight of the composition with an aqueous phase at a temperature from 60° C. to 75° C. in order to obtain an emulsion;
   (b) cooling the emulsion to a temperature from 48° C. to 55° C.;
   (c) adding to the emulsion an active phase comprising 0.05% to 3% by weight of at least one avermectin, relative to the total weight of the composition, wherein the at least one avermectin is dissolved in a medium comprising at least one glycol; and
   (d) cooling the emulsion to a temperature from 50° C. to 30° C.;
wherein the composition comprises 2% to 6% by weight of the at least one avermectin relative to the total weight of the composition.

2. The process according to claim 1, wherein (d) comprises cooling the emulsion at a cooling rate of from 0.5° C. to 1.5° C./5 min.

3. The process according to claim 1, wherein (d) comprises cooling the emulsion to a temperature selected from 42° C. to 47° C., and maintaining the temperature for 10 to 20 minutes; and further cooling the emulsion to a temperature from 30° C. to 40° C.

4. The process according to claim 1, wherein the at least one avermectin is selected from the group consisting of ivermectin and optical isomers thereof.

5. The process according to claim 1, wherein the at least one avermectin in the oily phase is in an amount from 2% to 3% by weight, relative to the total weight of the composition.

6. The process according to claim 2, wherein the cooling rate is from 0.8° C. to 1.5° C./5 min.

7. The process according to claim 2, wherein the cooling rate is 1° C./5 min.

8. The process according to claim 3, wherein the selected temperature is maintained for 15 minutes.

9. The process according to claim 1, wherein the at least one avermectin remains fully solubilized in the composition during manufacturing and for at least 1 month after manufacturing.

10. The process according to claim 1, wherein the at least one avermectin remains fully solubilized in the composition during manufacturing and for at least 2 months post-manufacture.

11. The process according to claim 1, wherein the at least one avermectin remains fully solubilized in the composition during manufacturing and for at least 3 months post-manufacture.

12. The process according to claim 1, wherein the at least one avermectin remains fully solubilized in the composition at temperatures between 5° C. to 40° C.

13. The process according to claim 1, wherein the glycol occurs in an amount between 0.5% to 15% by weight, relative to the total weight of the composition.

14. The process according to claim 13, wherein the glycol is 2% by weight, relative to the total weight of the composition.

15. The process according to claim 1, wherein the active phase represents between 1% to 18% of the total weight of the composition.

16. The process according to claim 1, wherein the active phase comprises an alcohol.

17. The process according to claim 16, wherein the glycol and the alcohol occur in a weight ratio between 1:4 to 4:1.

* * * * *